(12) United States Patent
Otagiri et al.

(10) Patent No.: US 7,351,800 B2
(45) Date of Patent: Apr. 1, 2008

(54) STABILIZED ALBUMIN PREPARATIONS

(75) Inventors: Masaki Otagiri, Kumamoto (JP); Toshiya Kai, Osaka (JP); Makoto Sato, Osaka (JP)

(73) Assignee: Nipro Corporation, Osaka (JP)

( * ) Notice: Subject to any disclaimer, the term of this patent is extended or adjusted under 35 U.S.C. 154(b) by 0 days.

(21) Appl. No.: 10/505,783

(22) PCT Filed: Feb. 28, 2003

(86) PCT No.: PCT/JP03/02320

§ 371 (c)(1),
(2), (4) Date: Aug. 26, 2004

(87) PCT Pub. No.: WO03/072123

PCT Pub. Date: Sep. 4, 2003

(65) Prior Publication Data

US 2005/0222024 A1 Oct. 6, 2005

(30) Foreign Application Priority Data

Feb. 28, 2002 (JP) ............... 2002-053337

(51) Int. Cl.
*C07K 1/00* (2006.01)
(52) U.S. Cl. .................................. 530/350
(58) Field of Classification Search ................. 530/350
See application file for complete search history.

(56) References Cited

U.S. PATENT DOCUMENTS 5,440,018 A   8/1995   Ohmura et al. ............. 530/363

FOREIGN PATENT DOCUMENTS

DE            0401379 B1 * 12/1989

| | | |
|---|---|---|
| EP | 0 374 625 A2 | 6/1990 |
| EP | 0 420 007 A1 | 4/1991 |
| EP | 0 570 916 A2 | 11/1993 |
| EP | 0 658 569 A1 | 6/1995 |
| EP | 0 699 687 A2 | 3/1996 |
| EP | 1 153 609 A1 | 11/2001 |

OTHER PUBLICATIONS

Ballou, Gerald et al., "The Heat Coagulation of Human Serum Albumin," *J. Biol. Chem.*, 153, 1944, pp. 589-605.
Boyer, Paul D. et al., "The Combination of Fatty Acids and Related Compounds with Serum Albumin," *J. Biol. Chem.*, 162, 1946, pp. 181-198.
Scatchard, G. et al., "Chemical, Clinical, and Immunological Studies on the Products of Human Plasma Fractionation. XXVI. the Properties of Solutions of Human Serum Albumin of Low Salt Content," *J. Clin. Invest.*, 24, 1945, pp. 671-679.
"Recombinant Albumin as a Pharmaceutical," *Clinical Molecular Medicine*, 1, 1993, pp. 939-943.

* cited by examiner

*Primary Examiner*—Karen Cochrane Carlson
*Assistant Examiner*—Agnes B. Rooke
(74) *Attorney, Agent, or Firm*—Kubovcik & Kubovcik

(57) ABSTRACT

This invention provides albumin preparations with safety and without any risk of side effects, which are free from viruses or contaminating proteins and can be stably stored over a long time while showing neither changes in appearance nor decrease in content.

There are provided a stabilized albumin preparation produced by uniformly mixing a medium-chain fatty acid or a salt thereof and a sulfur-containing amino acid or a derivative thereof with an aqueous albumin solution (e.g., a buffer such as phosphate buffer which can be administered as pharmaceutical preparations, injection water, or a physiological saline) and dissolving them therein, and then processing the mixture solution into a formulation suitable for parenteral administration such as an intravenous fluid preparation or an injectable solution, and a stabilization method for an albumin preparation.

10 Claims, 4 Drawing Sheets

MEDICAL AGENT UNDER TEST (1)

MEDICAL AGENT UNDER TEST (2)

MEDICAL AGENT UNDER TEST (3)

1: MERCAPTO TYPE   2: NON-MERCAPTO (DISULFIDE) TYPE   3: OXIDIZED TYPE

STABILIZED ALBUMIN PREPARATIONS

This application is a 371 of international application PCT/JP03/02320, which claims priority based on Japanese patent application No. 2002-053337 filed Feb. 28, 2002, which is incorporated herein by reference.

TECHNICAL FIELD OF THE INVENTION present invention relates to albumin preparations having excellent stability, and more particularly to albumin preparations such as those of a fractionated human serum albumin and a genetically engineered human serum albumin, which have excellent stability as well as safety.

BACKGROUND ART

For diseases based on acute hypoalbuminemia and chronic hypoalbuminemia which are hard to control, albumin preparations are used for improving clinical conditions by the supplementation thereof. Specifically, they are medical supplies indispensable for modern medical treatment because they are generally Used for correction of a circulating plasma volume in hemorrhagic and traumatic shock, improvement of edema, and various kinds of diseases such as liver cirrhosis and nephrotic syndrome (Peter T. Jr., The Plasma Proteins. Academic Press. New York. 133-81 (1975), Rosenorer V M., Rothschild M A., Albumin Structure, Function and Uses (1977)).

Conventionally, the production of human serum albumin preparations has been performed by fractionating blood collected from a human being and purifying the obtained albumin-containing aqueous solution according to various kinds of purification methods. The purification methods include an ethanol fractionation method, a PEG fractionation method, an ammonium sulfate fractionation method, a method in which the use of an anion exchanger is combined with heat treatment at 69° C. for 10 hours (JP 2-191226A), and a method in which treatment with an anion exchanger, treatment with a cation exchanger, and heat treatment at 60° C. for 10 hours are combined together (JP 3-17023A and JP 7-330626A) On the other hand, in recent years, the technology for mass production of albumin with a recombinant (gene recombination) has been established, and thus it has become possible to produce human albumin in large quantity by factory production without depending on blood donation (Clinical Molecular Medicine, 1, 939 (1993)).

In the production of albumin preparations (particularly, the production of fractionated human serum albumin), for removing a harmful virus unstable to heat and preventing contamination with a protein or the like, for example, a sterilization method such as low-temperature sterilization (60° C. for 10 hours) is used. In the low-temperature sterilization, N-acetyl tryptophan and sodium caprylate are added to human serum albumin (Ballou G A., Boyer P D., Luck J M., Lum F G., J. Biol. Chem., 153,589-605(1944), Scatchard G, Strong L E., Hughes W L. Jr., Ash Worth J N., Sparrow A H., J Clin. Invest., 24, 571-679 (1945), Boyer P D., Lum F G., Ballou G A., Luch J M., Rice R G., J.Biol. Chem., 162, 181-198 (1946)). However, the N-acetyl tryptophan has a side-effect problem such as intracerebral disease.

It is intended to provide albumin preparations with safety and without any risk of side effects, which are free from viruses or contaminating proteins and can be stably stored over a long time while showing neither changes in their appearance nor decrease in their content.

DISCLOSURE OF THE INVENTION

Under such circumstances, the inventors of the present invention have found that N-acetyl methionine exerts an excellent effect of stabilizing albumin and discovered that the N-acetyl methionine has an excellent effect of depressing agglomeration by coexisting with a medium-chain fatty acid. As a result of various studies on the basis of those findings, the present invention has been completed.

More specifically, the present invention relates to the following items 1) to 8):

1) A stabilized albumin preparation, characterized by comprising a medium-chain fatty acid or a salt thereof and a sulfur-containing amino acid or a derivative thereof;
2) The albumin preparation as claimed in item 1, wherein the medium-chain fatty acid is a straight-chain saturated fatty acid having 6 to 12 carbon atoms;
3) The albumin preparation as claimed in item 1, wherein the sulfur-containing amino acid is an amino acid having a mercapto group which may optionally be alkylated or may optionally be dimerized to a disulfide bond;
4) The albumin preparation as claimed in item 1, wherein the sulfur-containing amino acid derivative is an N-acylated sulfur- containing amino acid derivative;
5) The albumin preparation as claimed in item 1, wherein the total addition amount of the medium-chain fatty acid or a salt thereof and the sulfur-containing amino acid or the derivative is an approximately 1- to 20-fold molar quantity of albumin;
6) The albumin preparation as claimed in item 1, wherein the albumin is a genetically engineered human serum albumin;
7) A stabilizer for an albumin preparation, which comprises a medium-chain fatty acid or a salt thereof and a sulfur-containing amino acid or a derivative thereof; and
8) A stabilization method for an albumin preparation, characterized by comprising blending a medium-chain fatty acid or a salt thereof and a sulfur-containing amino acid or a derivative thereof.

In preparations according to the present invention, fractionated human serum albumin, genetically engineered human serum albumin, or the like is used as the effective ingredient albumin. The albumin preparation is used in the form of a solution generally having an albumin content of approximately 5 w/v % to approximately 25 w/v %. Solvents for dissolving albumin include water (injection water), a physiological saline, and buffers such as phosphate buffer which can be administered as pharmaceutical preparations.

Examples of medium-chain fatty acids to be added to the preparations of the present invention include fatty acids having 6 to 12 carbon atoms, preferably straight-chain saturated fatty acids having 6 to 12 carbon atoms. Preferable specific examples include caprylic acid, pelargonic acid, capric acid, undecanoic acid, and lauric acid. The salts of medium-chain fatty acids include basic salts such as alkali metal salts, for example, sodium salt and potassium salt. Among them, sodium caprylate is most preferable.

The sulfur-containing amino acids or derivatives thereof include amino acids having mercapto groups (SH groups) which may optionally be alkylated or may optionally be dimerized (a disulfide bond). The sulfur-containing amino acids include amino acids having 1 to 3 sulfur atoms in a molecule. Preferable specific examples thereof include cysteine, cystine, and methionine. The derivatives of sulfur-containing amino acids include N-acyl derivatives, preferably, for example, N-(alkanoyl having 1 to 6 carbon atoms) derivatives such as N-formyl, N-acetyl, N-propionyl, and N-butyryl, and, more preferably, N-acetyl derivatives. Among them, N-acetyl methionine is most preferable.

In the preparations of the present invention, the total addition amounts of the medium-chain fatty acid or the salt thereof and the sulfur-containing amino acid or the derivative thereof is preferably about an equimolar quantity to 20-fold molar quantity of albumin. Addition molar ratio of the added sulfur-containing amino acid or the derivative thereof: the added medium-chain fatty acid or the salt thereof is 0.1 to 10:1, preferably 0.5 to 2:1. One kind or two or more kinds of each of the medium-chain fatty acids or the salts thereof and the sulfur-containing amino acids or the derivatives thereof may be suitably mixed together in use.

In the preparations of the present inventions, if needed, a suitable amount of a pharmaceutically acceptable additive such as a colorant, a stabilizer, an antiseptic, a diluent, a pH regulator (e.g., basic amino acid, acidic amino acid, hydrochloric acid, acetic acid, malic acid, or sodium hydroxide), an osmolality regulator (e.g., an electrolyte such as sodium chloride, potassium chloride, potassium gluconate, magnesium sulfate, sodium bicarbonate, calcium chloride, calcium gluconate, or citric acid), or a surfactant (e.g., nonionic surfactant) may be added.

The pH value of a solution of the preparations of the present invention is adjusted to about pH 5 to 7.5, preferably about pH 6.5 to 7.4 by the addition of a pH regulator if required. The preparations of the present invention may further contain a physiologically active substance other than albumin when needed. For instance, saccharides (e.g., monosaccharides such as glucose and fructose, disaccharides such as maltose, and sugar alcohols such as sorbitol and xylitol) may be added.

The preparations of the present invention are used for therapeutic purposes, such as correction of a circulating plasma volume in hemorrhagic and traumatic shock, improvement of edema, and various kinds of diseases such as liver cirrhosis and nephrotic syndrome. They are generally administered to an adult in a dose of about 5 to 12.5 g at a time. The preparations of the present invention may be administered once or in about two to four portions a day depending on the disease condition.

The preparations of the present invention have almost no side effects with lower toxicity and safety, and they can be subcutaneously or intravenously administered to human beings and mammals (e.g., sheep, horses, and cows) according to methods known per se.

The preparations of the present invention can be prepared by uniformly mixing the medium-chain fatty acid or the salt thereof and the sulfur-containing amino acid or the derivative thereof with an aqueous albumin solution (e.g., a buffer such as phosphate buffer which can be administered as pharmaceutical preparations, injection water, or a physiological saline) and dissolving them therein, and then pharmaceutically processing the mixture solution into a formulation suitable for parenteral administration, such as intravenous fluid preparation or an injectable solution.

The medium-chain fatty acid or the salt thereof, the sulfur-containing amino acid or the derivative thereof, and albumin, which are used as raw materials, can be prepared by conventional methods or methods known per se.

Vessels for storing the resulting preparations include a glass vial and a plastic vessel made of polypropylene, polyethylene, or the like. The albumin preparations of the present invention can be filled in the above vessels or the like and hermetically sealed, and then subjected to sterilization (60° C./10 hours).

The preparations of the present invention show excellent stability because of little change in appearance and substantially no change in contents thereof even after sterilization under heat or long storage.

THE BEST MODE FOR CARRYING OUT THE INVENTION

Figure 1:
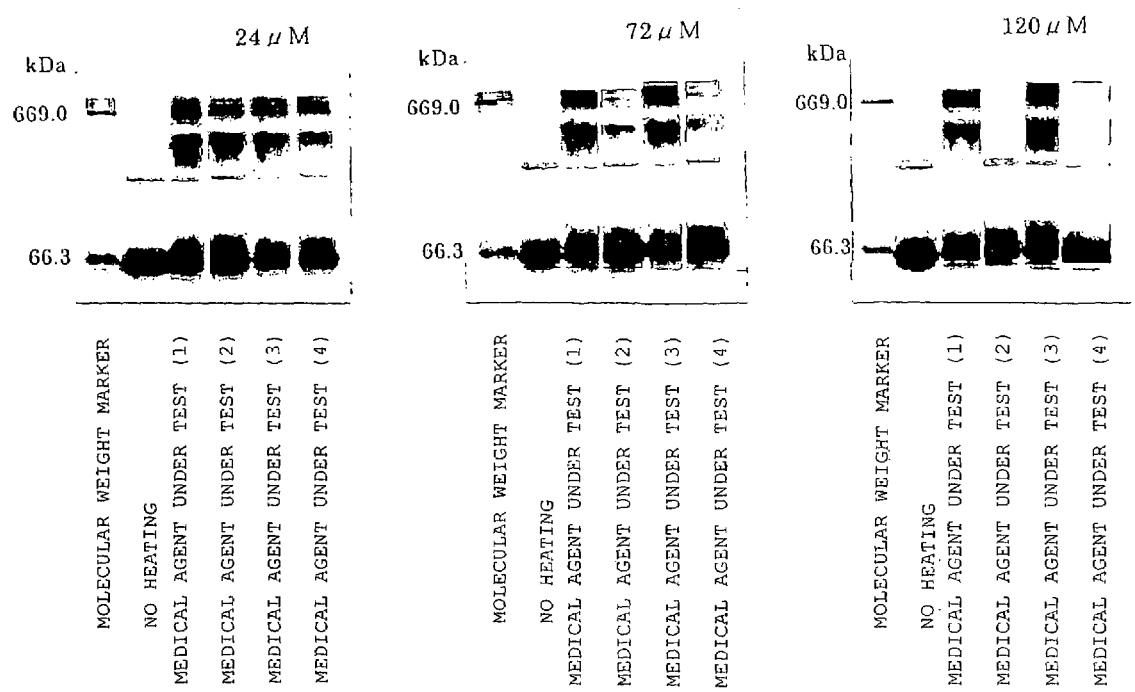
FIG. 1 An alternative photograph in place of a drawing for showing undenatured polyacrylamide gel electrophoresis of Experimental Example 2.

Hereinafter, the present invention will be explained concretely with reference to examples and experimental examples, but not limited to those examples.

EXAMPLE 1

Genetically engineered human serum albumin (hereinafter, human serum albumin will be abbreviated as HSA or albumin) was dissolved in a physiological saline to prepare 500 mL of an aqueous 25-w/v % HSA physiological saline solution. Then, 1662 mg of sodium caprylate and 1912.5 mg of N-acetyl methionine were added as stabilizers and dissolved therein, followed by hermetically sealing after dispensing the aqueous HSA physiological saline solution in an amount of 50 mL each into 50-mL vials.

EXAMPLE 2

HSA fractionated from blood was dissolved in a physiological saline to prepare 500 mL of an aqueous 25-w/v % HSA physiological saline solution. Then, 1662 mg of sodium caprylate and 1912.5 mg of N-acetyl methionine were added as stabilizers and dissolved therein, followed by hermetically sealing after dispensing the aqueous HSA physiological saline solution in an amount of 50 mL each into 50-mL vials.

EXPERIMENTAL EXAMPLE 1

1) Preparation of Medical Agent Under Test

Degreasing is performed on genetically engineered HSA by the method of Chen (Chen R F, J. Biol. Chem., 242, 173-181 (1967)). Furthermore, it was freeze-dried after dialysis and then used in all of the experiments described below.

Each of various medical agents was added to 100-μM HSA (1/15 mM phosphate buffer, pH 7.4) and then the following medical agents under test were prepared:

(1) a 100-μM HSA solution;
(2) a solution of 100-μM HSA+500-μM sodium caprylate;
(3) a solution of 100-μM HSA+500-μM N-acetyl methionine; and
(4) a solution of 100-μM HSA+500-μM N-acetyl methionine+500-μM sodium caprylate.

2) Measuring Method

The stabilization effect was evaluated in terms of a thermodynamic viewpoint by calculating a thermal transition temperature (Tm) and a change ΔHcal in enthalpy of transition from a differential scanning calorimetry (DSC) measurement on those medical agents under test (1) to (4). If the thermal transition temperature (Tm) increases, from the thermodynamic viewpoint, it means an increase in stability of the medical agents under test. In addition, if the change ΔHcal in enthalpy of transition increases, it means an increase in stability of the medical agents transition under test.

In Table 1, values of the thermal transition temperatures Tm, and values of the changes ΔHcal in enthalpy of transition of the respective medical agents under test (1) to (4) are shown. Those values were analyzed by a DSC thermogram of the HSA solution. Differential scanning calorimetry (DSC method)

For the DSC, measurement was made using the MC-2 differential scanning calorimeter manufactured by MicroCal Co., Ltd. The measuring conditions are shown below.

Scanning rate: 1 K/min.
Albumin content: 100 μM Solvent: 1/15 M phosphate buffer (pH 7.4)

Reversibility of thermal denaturation was confirmed by cooling the albumin solution after first measurement and then heating the albumin solution again. As a result, it was found that the albumin caused reversible thermal transition without bringing about irreversible denaturation as far as it was heated up to 85° C. or less. The resulting thermogram was subjected to fitting using a nonlinear fitting algorithm (Using Origin TM scientific plotting software), followed by analysis as described below by the use of a lower area of the resulting excess thermal capacity curve.

Change in enthalpy of transition $\Delta Hcal = \int Cex \, dT$ wherein Cex represents an excess thermal capacity.

3) Results

As is evident from Table 1, an increase in thermal transition temperature (Tm) was confirmed in each of the solutions with the additions of various medical agents, compared with an HSA solution without the addition of any medical agent. The addition of sodium caprylate leads to about a 7° C. increase in Tm of albumin, so that an increase in stability thereof to heat was shown.

In addition, the addition of N-acetyl methionine alone allowed a slight increase in Tm and an increase in change ΔHcal in enthalpy transition.

The solution added with sodium caprylate and N-acetyl methionine was in a conformational state in which albumin was placed in a more methodical fashion, and thus it was found that the state is more stable than the native state.

TABLE 1

| Medical Agent under test | Tm (° C.) | Δhcal ($10^5$ kcal/mol) |
| --- | --- | --- |
| (1) HSA | 59.50 | 1.64 |
| (2) HSA + sodium caprylate | 66.83 | 2.1 |
| (3) HSA + N-acetyl methionine | 60.60 | 1.81 |
| (4) HSA + sodium caprylate + N-acetyl methionine | 66.51 | 2.03 |

EXPERIMENTAL EXAMPLE 2

1) Preparation of Medical Agents Under Test

A 24-μM HSA phosphate buffer (67 mM, pH 7.4) was prepared and various medical agents were added thereto so as to have concentrations of 24, 72, or 120 μM to make medical agents under test (1) to (4) for examining the influence on the concentration of the medical agent added on the stabilization effect:

(1) 24-μM HSA;
(2) 24-μM HSA+sodium caprylate;
(3) 24-μM HSA+N-acetyl methionine; and
(4) 24-μM HSA+N-acetyl methionine+sodium caprylate.

2) Measuring Method

The thermal stability with sterilization under heat at 60° C. for 30 minutes was evaluated by means of NATIVE-PAGE.

NATIVE-PAGE

NATIVE-PAGE was conducted using a 7.5% (w/v) polyacrylamide gel in accordance with the Davis method. Proteins were stained with Coomassie brilliant blue R-250 and the following proteins were used as molecular weight markers:

α-thyroglobulin (M. W. 669000), ferritin (M. W. 443000), lactate dehydrogenase (M. W. 139850), bovine serum albumin (M. W. 66267), and trypsin inhibitor (M. W. 20110) were used.

3) Results

The results of NATIVE-PAGE are shown in FIG. 1. After the heat treatment at 60° C. for 30 minutes, a large quantity of aggregates was confirmed in the medical agent under test (1) (no medical agent added). On the other hand, the aggregate-inhibition effects were confirmed in the medical agent under test (2) (containing sodium caprylate), the medical agent under test (3) (containing N-acetyl methionine), or the medical agent under test (4) (containing sodium caprylate and N-acetyl methionine), respectively. With respect to their concentration dependence, as was evident from migration patterns, almost no aggregate-inhibition effect was confirmed when the medical agent was added at an equimolar concentration to albumin. However, a distinct aggregate-inhibition effect was observed by the addition in 3-fold concentration (72 μM) and a remarkable aggregate-inhibition effect was observed by the addition in 5-fold concentration (120 μM).

EXPERIMENTAL EXAMPLE 3

Figure 2:
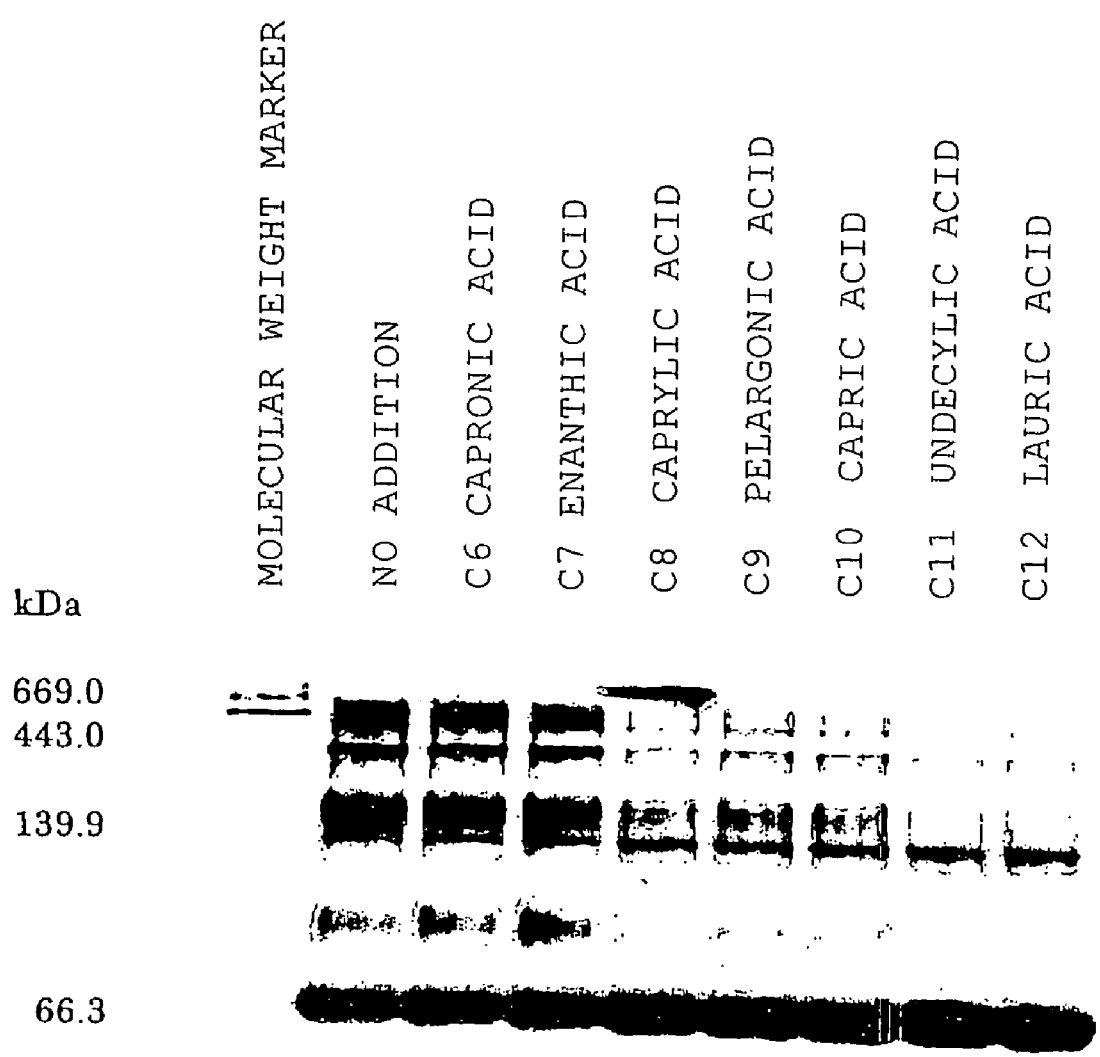
FIG. 2 An alternative photograph in place of a drawing for showing undenatured polyacrylamide gel electrophoresis of Experimental Example 3.

The aggregate-inhibition effect under heat was examined using medium-chain fatty acids except sodium caprylate (electrophoresis in FIG. 2). The measurement samples used were such that 5-fold concentrations (120 μM) of the respective fatty acids were each added to a 24-μM HSA phosphate buffer (67 mM, pH 7.4).

As a result, the aggregate-inhibition effect was slightly observed in caproic acid (C6) and enanthic acid (c7) having a carbon chain shorter than that of sodium caprylate and remarkable inhibition effects were observed in fatty acids having carbon chains not shorter than that of sodium caprylate, respectively.

EXPERIMENTAL EXAMPLE 4

1) Preparation of Medical Agents Under Test

A 24-μM HSA phosphate buffer (64 mM, pH 7.4) was prepared and then medical agents under test were prepared as described below by the addition of various medical agents at a concentration of 120 μM, followed by adding 2,2'-azobis-(2-amidino-propane) dihydrochloride (hereinafter referred to as AAPH) (first grade, manufactured by Wako Pure Chemical Industries, Ltd.) to 5 mL of the medical agent under test so as to have a final concentration of 10 μM:
(1) HSA;
(2) HSA+sodium caprylate; and
(3) HSA+sodium caprylate+N-acetyl methionine 2) Measurement of Abundance Ratio Between Mercapto Type and Non-mercapto Type of HSA The abundance ratio (mercapto fraction) between the mercapto type and non-mercapto type of HSA was determined using high performance liquid chromatography (hereinafter, referred to as HPLC).

The device for HPLC used for the measurement of mercapto fraction was the Shimadzu LC-4A equipped with a gradient device and connected to the Shimadzu SPD-24SUV detector and the Shimadzu C-R2AX data-processing device. Elution of the sample was performed using a method of a linear gradient from (A) a 0.05-M tris-acetate buffer (pH 7.0) to (B) a 0.05-M tris-acetate buffer (pH7.0) containing 0.5-M sodium acetate for 30 minutes at a flow rate of 0.5 mL/min. The sample was detected using 280-nm UV at room temperature.

3) Results

Figure 3:
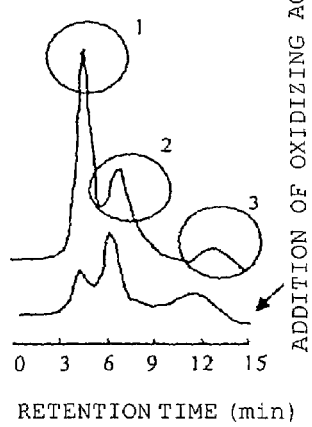
FIG. 3 A diagram showing an HPLC chromatogram of Experimental Example 4.
Figure 3:
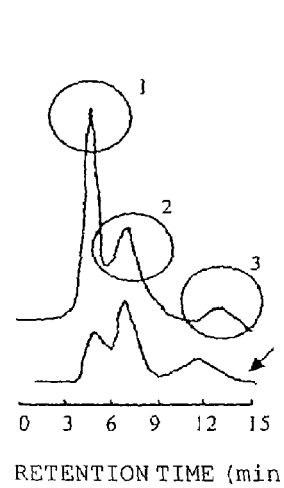
Figure 3:
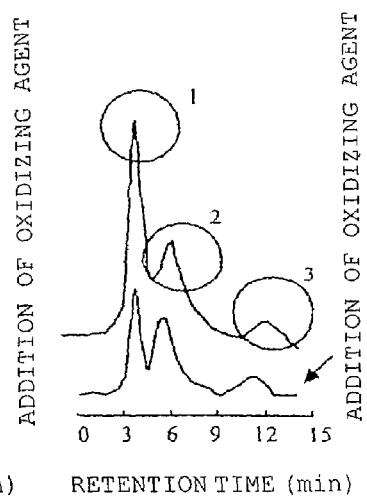

A HPLC chromatogram of HSA in the medical agent under test (1) is shown in FIG. 3. In the medical agent under test (1), a decrease in mercapto type and an increase in non-mercapto type were observed.

A change in abundance ratio between the mercapto type and non-mercapto type of HSA could not be confirmed even after the addition of sodium caprylate. However, the medical agent under test (3) (concomitant use of sodium caprylate and N-acetyl methionine) inhibits a change in abundance ratio therebetween significantly and an antioxidative effect was confirmed. Therefore, it is concluded that N-acetyl methionine without side effects is suitable as a stabilizer.

EXPERIMENTAL EXAMPLE 5

Figure 4:
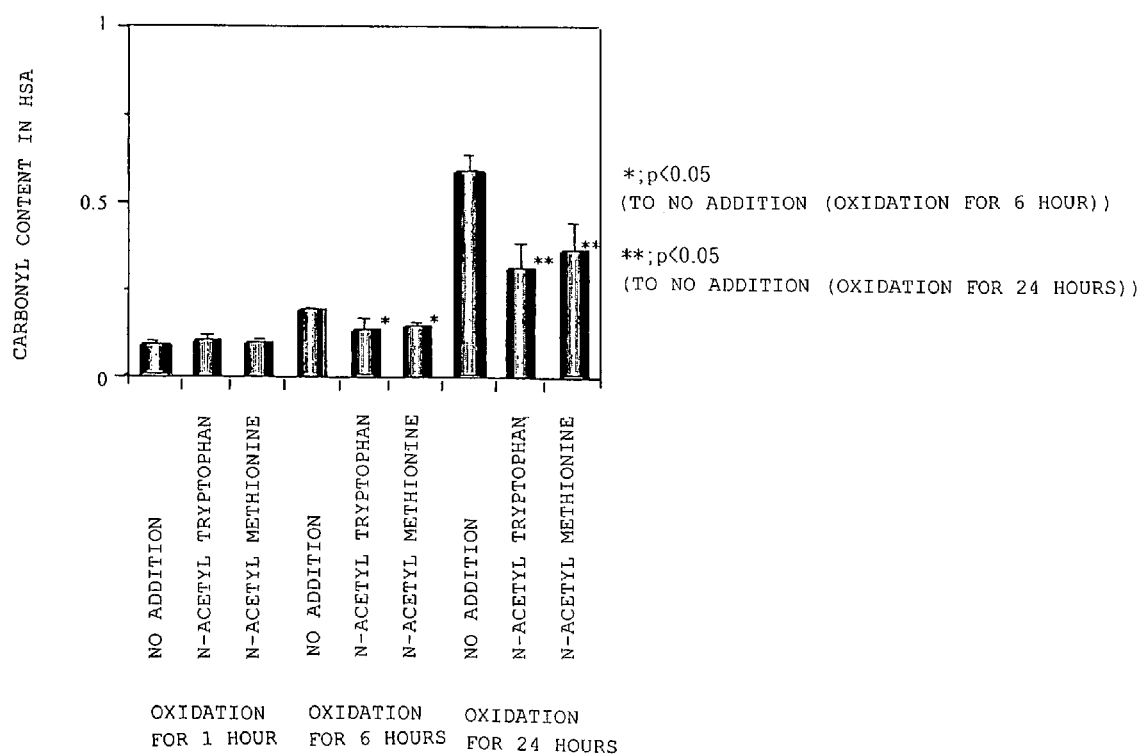
FIG. 4 A diagram showing carbonyl content in HSA with oxidation of Experimental Example 5.

An excess amount of an oxidizing agent, 2,2'-azobis-(2-amidinopropane) dihydrochloride (AAPH) was added to HSA to oxidize the HSA. After the oxidation for a predetermined time, the carbonyl content in HSA was determined. From the relationship between the oxidizing time and the type of a stabilizer, the anti-oxidation actions of various stabilizers were evaluated (FIG. 4). The carbonyl content, which indicates the degree of oxidation, was determined in accordance with the method of Climent et al. (described in Climent I., Thai L., and Levine R L., Anal Biochem. 182, 226 (1989)) and represented as a modification amount per protein of a carbonyl-coloring reagent, Fluorsceinamine.

In the case of N-acetyl methionine, a significant decrease in carbonyl content was observed in comparison with the medical agent under test without addition. Thus, it is clear that the anti-oxidation action can be obtained.

EXPERIMENTAL EXAMPLE 6

Using a physiological saline and genetically engineered HSA, 500 mL of a 25-w/v % solution was prepared. Then, 1662 mg of sodium caprylate and 1912.5 mg of N-acetyl methionine were added as stabilizers thereto to prepare the medical agents under test, followed by hermetically sealing 50 mL of the agent in a vial. In addition, the genetically engineered HSA without a stabilizer was prepared with a physiological saline in a concentration of 25 w/v %, followed by hermetically sealing 50 mL of the resultant in a vial.

Those samples were subjected to heat treatment under sterilization conditions of 60° C. for 30 minutes, and then the generation of contaminants was visually observed. As a result, in the sample without the addition of the additive, the generation of albumin aggregates by heat was distinctly observed. On the other hand, no contaminant was observed in the sample with the addition of the stabilizer.

INDUSTRIAL APPLICABILITY

The stabilized albumin preparations of the present invention can be safely stored for a long term in a stable manner without risk of side effects. In the case of the addition of medium-chain fatty acid or the salt thereof alone, a thermal stabilization effect can be observed but the anti-oxidization action of albumin is small. In the case of the addition of sulfur-containing amino acid or the derivative thereof alone, no thermal stabilization effect on albumin is observed. Therefore, the addition of both the medium-chain fatty acid or the salt thereof and the sulfur-containing amino acid or the derivative thereof synergistically provides an excellent albumin stabilization effect.

The invention claimed is:

1. An albumin preparation, characterized by comprising a medium-chain fatty acid or a salt thereof and a sulfur-containing amino acid or a derivative thereof selected from the group consisting of cystine, methionine, N-acylated cysteine, N-acylated cystine and N-acylated methionine
   wherein the total addition amount of the medium-chain fatty acid or salt thereof and the sulfur-containing amino acid or derivative thereof is in the range of equimolar quantity to 20-fold molar quantity of the albumin, and
   further wherein the molar ratio of the sulfur-containing amino acid or derivative thereof to the medium-chain fatty acid or salt thereof is 0.1:1 to 10:1.

2. The albumin preparation as claimed in claim 1, wherein the medium-chain fatty acid is a straight-chain saturated fatty acid having 6 to 12 carbon atoms.

3. The albumin preparation as claimed in claim 1, wherein the sulfur-containing amino acid derivative is N-acetyl methionine.

4. The albumin preparation as claimed in claim 1, wherein the albumin is a genetically engineered human serum albumin.

5. A stabilization method for an albumin preparation, characterized by comprising blending a medium-chain fatty acid or a salt thereof and a sulfur-containing amino acid or a derivative thereof selected from the group consisting of cystine, methionine, N-acylated cysteine, N-acylated cystine and N-acylated methionine
   wherein the total addition amount of the medium-chain fatty acid or salt thereof and the sulfur-containing amino acid or derivative thereof is in the range of equimolar quantity to 20-fold molar quantity of the albumin, and
   further wherein the molar ratio of the sulfur-containing amino acid or derivative thereof to the medium-chain fatty acid or salt thereof is 0.1:1 to 10:1.

6. A stabilized protein preparation for administration to humans and other mammals comprising a protein which is albumin, a medium-chain fatty acid or a salt thereof and a sulfur-containing amino acid or a derivative of a sulfur-containing amino acid selected from the group consisting of N-acylated cysteine, N-acylated cystine and N-acylated methionine wherein the total addition amount of the medium-chain fatty acid or salt thereof and the sulfur-containing amino acid or derivative thereof is in the range of equimolar quantity to 20-fold molar quantity of the albumin, and further wherein the molar ratio of the sulfur-containing amino acid or derivative thereof to the medium-chain fatty acid or salt thereof is 0.1:1 to 10:1.

7. The protein preparation as claimed in claim 6, wherein the medium-chain fatty acid is a straight-chain saturated fatty acid having 6 to 12 carbon atoms.

8. The protein preparation as claimed in claim 6, wherein the sulfur-containing amino acid derivative is N-acetyl methionine.

9. The protein preparation as claimed in claim 6, wherein the albumin is a genetically engineered human serum albumin.

10. A stabilizer for a protein preparation for administration to humans and other mammals, where the protein is albumin, which comprises a medium-chain fatty acid or a salt thereof and a sulfur-containing amino acid or a derivative of a sulfur-containing amino acid selected from the group consisting of N-acylated cysteine, N-acylated cystine and N-acylated methionine wherein the total addition amount of the medium-chain fatty acid or salt thereof and the sulfur-containing amino acid or derivative thereof is in the range of equimolar quantity to 20-fold molar quantity of the albumin, and further wherein the molar ratio of the sulfur-containing amino acid or derivative thereof to the medium-chain fatty acid or salt thereof is 0.1:1 to 10:1.

* * * * *